(12) United States Patent
Chaume et al.

(10) Patent No.: US 9,470,659 B2
(45) Date of Patent: Oct. 18, 2016

(54) DEVICE AND METHOD FOR DETECTING AN IMPACT ON A COMPOSITE MATERIAL STRUCTURE

(71) Applicant: Airbus Operations (SAS), Toulouse (FR)

(72) Inventors: Olivier Chaume, Toulouse (FR); Xavier Kern, Toulouse (FR); Jean-Pascal Cabot, Toulouse (FR)

(73) Assignee: AIRBUS OPERATIONS SAS, Toulouse (FR)

( * ) Notice: Subject to any disclaimer, the term of this patent is extended or adjusted under 35 U.S.C. 154(b) by 373 days.

(21) Appl. No.: 14/109,598

(22) Filed: Dec. 17, 2013

(65) Prior Publication Data

US 2014/0165728 A1  Jun. 19, 2014

(30) Foreign Application Priority Data

Dec. 18, 2012 (FR) ..................................... 12 62207

(51) Int. Cl.
*G01N 29/04* (2006.01)
*G01N 29/24* (2006.01)

(52) U.S. Cl.
CPC ............ *G01N 29/04* (2013.01); *G01N 29/045* (2013.01); *G01N 29/2475* (2013.01); *G01N 29/2481* (2013.01); *G01N 2291/0231* (2013.01); *G01N 2291/2694* (2013.01)

(58) Field of Classification Search
CPC ........... G01N 29/045; G01N 29/2475; G01N 29/04; G01N 29/2481; G01N 2291/0231; G01N 2291/2694
USPC .......................................................... 73/584
See application file for complete search history.

(56) References Cited

U.S. PATENT DOCUMENTS

| 6,370,964 | B1 | 4/2002 | Chang et al. |
| 7,235,914 | B2* | 6/2007 | Richards ................. F02B 75/34 310/324 |
| 7,930,112 | B2* | 4/2011 | Mattes ................ G01M 5/0016 702/36 |
| 8,447,530 | B2* | 5/2013 | Pado ..................... G01M 7/025 702/36 |
| 8,594,882 | B2* | 11/2013 | Wilke .................... G07C 5/008 701/29.1 |
| 8,766,511 | B2* | 7/2014 | Duce ................... H01L 41/1132 310/319 |
| 8,886,388 | B2* | 11/2014 | Moser ................. G01M 5/0033 701/29.1 |
| 2007/0017297 | A1 | 1/2007 | Georgeson et al. |
| 2007/0100582 | A1 | 5/2007 | Griess et al. |

OTHER PUBLICATIONS

French Search Report, May 29, 2013.
A Technical Framework and Roadmap of Embedded Diagnostics and Prognostics for Complex Mechanical Systems in Prognostics and Health Management Systems, Chen et al., Jun. 1, 2012.

* cited by examiner

*Primary Examiner* — J M Saint Surin
(74) *Attorney, Agent, or Firm* — Greer, Burns & Crain, Ltd.

(57) ABSTRACT

A device for detecting an impact on a composite material structure. This detection device comprises at least two acoustic modules intended to be secured to the composite material structure and a processing unit able to communicate remotely with each of the acoustic modules. Each acoustic module is electrically autonomous and comprises its own means for recording the sound waves sensed by its acoustic sensor. An aircraft structure is also provided comprising a composite material structural element equipped with the impact detection device. A method is also provided for detecting an impact on a composite material aircraft structural element equipped with an impact detection device.

13 Claims, 1 Drawing Sheet

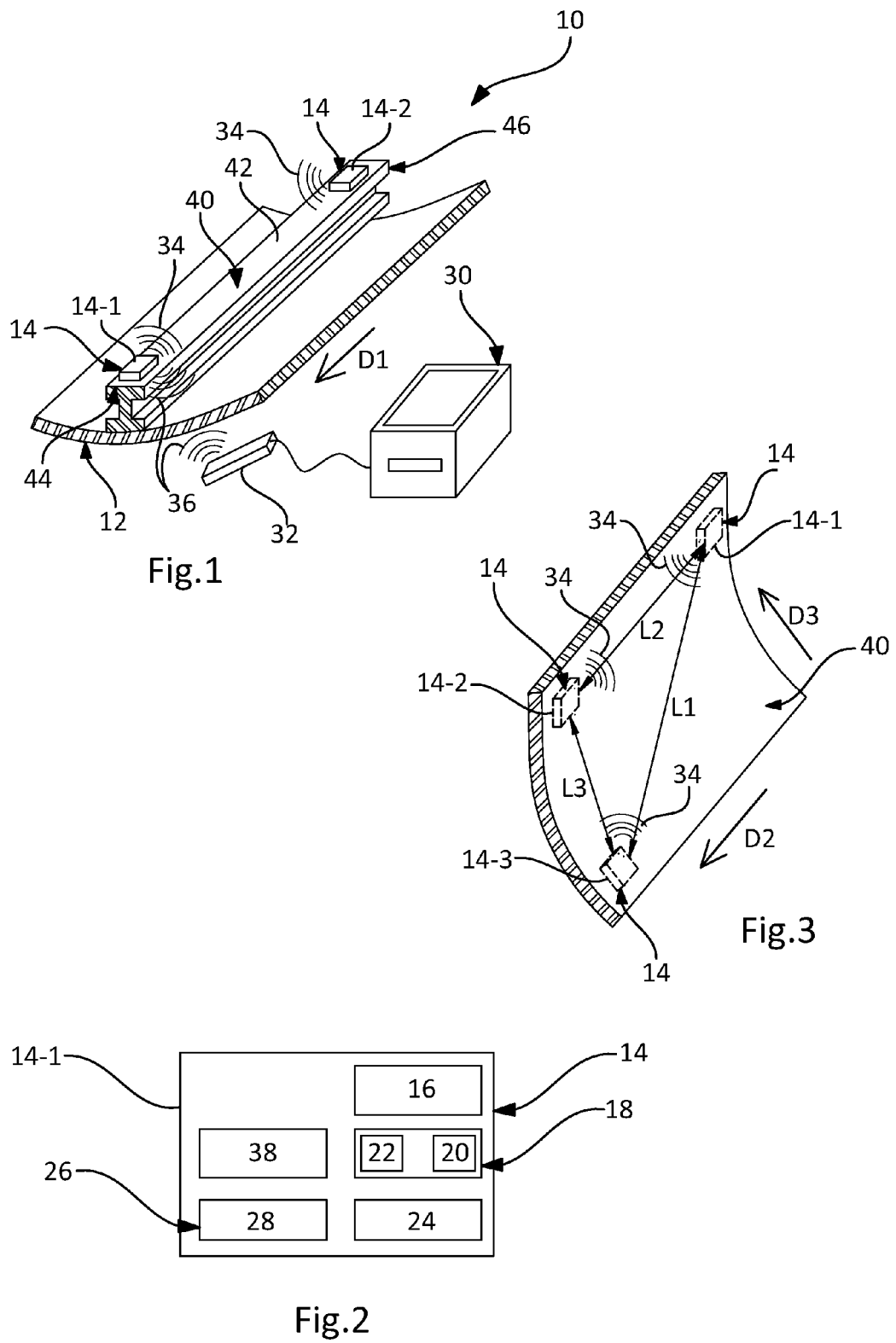

DEVICE AND METHOD FOR DETECTING AN IMPACT ON A COMPOSITE MATERIAL STRUCTURE

CROSS-REFERENCES TO RELATED APPLICATIONS

This application claims the benefit of the French patent application No. 12 62207 filed on Dec. 18, 2012, the entire disclosures of which are incorporated herein by way of reference.

BACKGROUND OF THE INVENTION

The present invention relates to a device and to a method for detecting an impact on a composite material structure.

Composite materials are widely used in aeronautics, including for making the elements of the primary structure of the aircraft constituting the fuselage.

During a flight, or while the aircraft is being parked, these exterior structural elements are apt to undergo diverse impacts.

It is therefore necessary to undertake a check of these exterior structural elements regularly, and preferably before each new use of the aircraft.

This check is performed by searching for any damage due to impacts on these structural elements.

Since this check has to be performed on all these elements, it is lengthy and tedious.

Moreover, it is not sufficient to carry out a visual check of these structural elements.

Indeed, a composite material structure that has received an impact may be damaged inside, for example by delamination, while exhibiting an exterior aspect similar to that of an intact structure.

Hence, in the case of suspicion of damage and periodically, provision is generally made for an ultrasound-based check on the integrity of the exterior structural elements, this type of conventional check making it possible to detect damage inside a composite material structure.

According to a first drawback, this conventional ultrasound-based check remains a lengthy and tedious operation, the emitting probe having to be moved over all the exterior structural elements to be checked.

Moreover, certain zones of these exterior structural elements are difficult to access and therefore difficult to check.

According to another drawback, for certain levels of impact energy, accidental delaminations remain invisible with these conventional non-destructive checking means.

Consequently, plies are added to the composite material structure during the design of these exterior structural elements so as to guarantee their resilience in the presence of defects that cannot be detected with conventional non-destructive checking means.

These additional plies increase the overall weight of the aircraft and penalize its performance.

Hence, a need exists for a device and for a non-destructive method making it possible to identify and to locate an impact in a composite material structure, and also making it possible to determine the energy level of the impact so as to evaluate its criticality.

Hence, an installation for detecting and analyzing the damage undergone by the fuselage of an aircraft while parked is known from patent FR-2,937,953.

More particularly, this installation is intended to monitor the opening of a door or of a hatch for access to the internal volume of the aircraft.

For this purpose, this installation comprises:

an array of sensors of the piezoelectric type installed around this opening on the internal face of the fuselage, and able to sense mechanical vibrations propagating in the structure of the fuselage around the opening and to produce electrical signals representative of the mechanical vibrations sensed, a processing unit connected electrically by wire to the array of sensors, and able to ensure the recording of the electrical signals produced by the sensors and to digitally process them so as to detect a strike on the fuselage around the opening, and so as to determine whether this strike is damaging, and if such is the case, to locate the latter, a local alarm situated near the door, connected electrically by wire to the processing unit and activated by the latter when the strike is damaging, a data concentrator connected electrically by wire to the processing unit, the concentrator being able to collect the alarm data originating from the processing unit and to transmit them electrically by wire to a centralized display, a centralized display intended to be connected electrically by wire to the data concentrator, able to display for each opening an alarm state, and if a damaging strike is detected, an item of information relating to the location of the strike.

Generally, the installation which is described in this document FR-2,937,953 is not suited to the detection of an impact on a composite material structure since it has been developed for sheet metal aircraft fuselages.

Then, the installation disclosed in this document FR-2,937,953 is only intended to be active when the aircraft is on the ground and at rest. Therefore, it does not make it possible to detect impacts on the exterior structural elements when the aircraft is in flight.

Moreover, in the installation disclosed in this document FR-2,937,953, the sensors of the piezoelectric type are linked by wire to the processing unit, which is itself linked by wire to the data concentrator, itself connected by wire to a centralized display provided to be installed in the flight deck.

Consequently, the entirety of the detection installation must be integrated into the aircraft right from its design and its assembly, thereby preventing any use of this installation on existing aircraft, without dismantling numerous elements and providing numerous hours of labor.

SUMMARY OF THE INVENTION

Hence, the present invention is aimed at alleviating the drawbacks of the prior art.

For this purpose, the subject of the invention is a device for detecting an impact on a composite material structure, this detection device comprising at least two acoustic modules intended to be secured to the composite material structure and a processing unit able to communicate remotely with each of the acoustic modules.

According to the invention, each acoustic module comprises an acoustic sensor, electrical energy generating means, means for recording the sound waves sensed by its acoustic sensor, and remote communication means configured to communicate with the processing unit.

By virtue of the remote communication means of the acoustic modules, it is not necessary to provide the processing unit in the aircraft, and the sound waves recorded during a flight of the aircraft can be recovered remotely by the processing unit, thereby facilitating the aircraft checking and maintenance operations.

Moreover, by virtue of the autonomy of the acoustic modules, it is not absolutely necessary to integrate the detection device into the aircraft right from its design and its assembly, and therefore the integration of the detection device on an existing aircraft is facilitated.

Preferably, the electrical energy generating means of each acoustic module comprise a micro-kinetic generator.

For the implementation of the detection device, at least one acoustic module, called the master module, comprises a clock.

And, still for the implementation of the detection device, the remote communication means of the master acoustic module are configured to communicate with the other acoustic modules of the detection device.

The present invention also covers an aircraft structure comprising a composite material structural element equipped with an impact detection device.

The acoustic modules can be fastened to a surface of the structural element, and/or provided in the structural element.

In greater detail, when the structural element extends principally in one dimension, the detection device comprises only a first acoustic module secured to a first end of the structural element, and a second acoustic module secured to a second end of the structural element.

Whereas, when the structural element extends principally in two dimensions, the detection device comprises at least three acoustic modules secured to the structural element, the distances separating the modules pairwise from among the at least three modules all being different.

Finally, the present invention also covers a method for detecting an impact on a structural element equipped with an impact detection device.

This detection method implements the detection device according to the following steps:

emission by the communication means of a master acoustic module of a radiofrequency signal comprising a time base common to the set of modules of the device towards the other acoustic modules of the device, recording by the recording means of each acoustic module of the sound waves travelling through the structural element over a determined duration, transfer of the sound waves recorded by each acoustic module to the processing unit, and analysis of the transferred sound waves so as to detect any impacts occurring on the structural element.

Advantageously, the step of analyzing the transferred sound waves makes it possible to evaluate the criticality of an impact occurring on the structural element and/or to locate an impact occurring on the structural element.

Unlike the device of the prior art, the detection device according to the invention can be implemented during a flight of the aircraft.

BRIEF DESCRIPTION OF THE DRAWINGS

Other characteristics and advantages will emerge from the description which follows of the invention, description given by way of example only, with regard to the appended drawings in which:

FIG. 1 is a partial perspective view of a composite material longilinear structural element equipped with an impact detection device, this view illustrating the invention, FIG. 2 is a schematic representation of an acoustic module of an impact detection device, this schematic representation illustrating the invention, FIG. 3 is a partial perspective view of a composite material planiform structural element equipped with an impact detection device, this view illustrating the invention.

DETAILED DESCRIPTION OF THE PREFERRED EMBODIMENTS

As illustrated by FIG. 1, the present invention relates to a device 10 for detecting an impact on a composite material structure 12.

The detection device 10 comprises at least two acoustic modules 14 intended to be secured to the composite material structure 12, and a processing unit 30 able to communicate remotely with each of the acoustic modules 14.

As illustrated schematically by FIG. 2, each acoustic module 14 comprises an acoustic sensor 16.

Thus, each acoustic module 14 is capable of sensing the sound wave (or waves), especially of Dirac type, generated by an impact on the structure 12 and propagating in this structure 12.

In a first variant, the acoustic sensor 16 is of piezoelectric type.

In a second variant, the acoustic sensor 16 is of electromagnetic type and comprises for example a solenoid with a central magnet.

According to the invention, each acoustic module 14 is electrically autonomous.

Thus, since no wired link has to be provided between the modules 14, or in between a module 14 and another entity of the detection device 10, it is possible to envisage integration of the detection device 10 into an existing composite material structure 12, and for example into a composite material structural element of an aircraft already in service.

With a view to being electrically autonomous, each acoustic module 14 comprises electrical energy generating means 18.

Preferably, the electrical energy generating means 18 of an acoustic module 14 comprise a micro-kinetic generator 20.

A micro-kinetic generator 20 such as this makes it possible to produce electrical energy on the basis of the vibrations undergone by the structure 12, especially when this structure 12 belongs to an aircraft and when this aircraft is in flight.

Of course, the electrical energy generating means 18 also comprise an accumulator 22 for storing up the electrical energy produced by the micro-kinetic generator 20.

Advantageously, each acoustic module 14 is made using low energy consumption CMOS technology.

Then, each acoustic module 14 comprises means 24 for recording the sound waves sensed by its acoustic sensor 16.

Thus, each acoustic module 14 is able to record for a recording cycle of determined duration the sound waves travelling through the composite material structure 12, and for example the sound waves travelling through a composite material structural element of an aircraft while this aircraft is in flight.

Advantageously, these recording means 24 take the form of a resettable memory.

Thus, the recording means 24 offer a maximum recording capacity at the start of each new recording cycle, and for example before each take-off of an aircraft.

For the operation of the detection device, each acoustic module 14 comprises remote communication means 26 configured to communicate with the processing unit 30.

These remote communication means 26 preferably take the form of a radiofrequency transceiver 28 working in the high frequencies.

These remote communication means 26 allow the various acoustic modules 14 of a detection device 10 to communicate with the processing unit 30, but also to communicate with one another so as to synchronize their operation.

Indeed, these remote communication means 26 make it possible to export to the processing unit 30 the data relating to the sound waves recorded by each acoustic module 14 during a recording cycle, such as for example the sound waves recorded in a composite material structural element of an aircraft while the aircraft is in flight.

Hence, as illustrated in FIG. 1, the processing unit 30 is autonomous and transportable.

Preferably, the communication between the processing unit 30 and each acoustic module 14 is performed by way of a radiofrequency reader 32 linked by wire to the processing unit 30.

Indeed, although the processing unit 30 is transportable, it is easier to move a radiofrequency reader 32 in proximity to each acoustic module 14.

This processing unit 30 makes it possible, by way of a radiofrequency signal 36, to recover remotely from the composite material structure 12 the data relating to the sound waves recorded by each acoustic module 14 during a recording cycle.

In the case of a composite material structural element of an aircraft, the remote communication between the processing unit 30 and the acoustic modules 14, and in a more general manner the detection device 10, makes it possible to recover from the exterior of the aircraft the data relating to the sound waves recorded by each module 14 during a flight.

Therefore, in the present invention, only the acoustic modules 14 are permanently present in the composite material structure 12 to be monitored, i.e., in the structure of an aircraft in the application envisaged.

Finally, at least one acoustic module 14-1, called the master module, of the detection device 10 comprises a clock 38.

This clock 38 is used for the synchronization of the operation during a recording cycle of the various acoustic modules 14 secured to the composite material structure 12, i.e., for the synchronization of the operation of the modules secured to one and the same aircraft composite material structural element during a flight of the aircraft.

To carry out this synchronization, the remote communication means 26 of the master acoustic module 14-1 are configured to communicate with the other acoustic modules 14-2,14-3 of the detection device 10.

In greater detail, the master acoustic module 14-1 sends to the other modules 14-2,14-3, by way of its remote communication means 26, a radiofrequency signal 34 comprising a time base common to all the modules 14-1,14-2,14-3, as illustrated by FIGS. 1 and 3.

The sending of this synchronization signal 34 announces the start of a recording cycle, for example at the moment of takeoff of an aircraft.

Advantageously, a signal for verifying and correcting the synchronization of the modules 14-1,14-2,14-3 can be sent at a frequency determined by the master module 14-1 for the duration of a recording cycle, i.e., for example for the duration of a flight of an aircraft comprising a composite material structural element equipped with a detection device 10.

As illustrated by FIGS. 1 and 3, the present invention also relates to an aircraft structure 12 comprising a composite material structural element 40 equipped with an impact detection device 10.

In a first variant layout of the modules illustrated by FIG. 1, two acoustic modules 14-1,14-2 are fastened to a surface 42 of the structural element.

Preferably, an acoustic module 14 of a detection device 10 is fastened to a structural element 40 by gluing.

Alternatively, an acoustic module 14 can be fastened to a structural element 10 by any mechanical link permitting rapid linking and allowing the acoustic sensor 16 to appropriately sense the sound waves travelling through the structural element 40.

This first variant layout of the modules 14 permits use of the detection device 10 on an aircraft already in service.

In a second variant layout of the modules illustrated by FIG. 3, three acoustic modules 14-1,14-2,14-3 are provided in the structural element 40, and for example integrated into this structural element 40 during its manufacture.

This second variant is made possible by the autonomous operation of the modules 14.

This second variant layout of the modules 14 does not necessarily require integration of the detection device 10 into the aircraft during its design and assembly.

Indeed, it is merely necessary to replace in the structure 12 of the aircraft the existing structural element with a structural element 40 in which the acoustic modules 14 are implanted, doing so without any wired connection additional to those already present in the aircraft.

The invention also covers a third variant combining the layouts provided in the first and second variants hereinabove, and in which at least one acoustic module 14 is fastened to a surface 42 of a structural element 40, and at least one acoustic module 14 is provided in the structural element 40.

The invention also provides for various implementations of the detection device 10 as a function of the design of the structural element 40.

Thus, as illustrated in FIG. 1, when the structural element 40 extends principally in one dimension D1, the detection device 10 comprises only a first acoustic module 14-1 secured to a first end 44 of the structural element 40, and a second acoustic module 14-2 secured to a second end 46 of the structural element 40.

Indeed, in the case of a longilinear structural element 40, i.e., one which extends in a single dimension D1, two acoustic modules 14-1,14-2 suffice to allow the detection, location and evaluation of an impact.

However, as illustrated in FIG. 3, when the structural element 40 extends principally in two dimensions D2,D3, the detection device 10 comprises at least three acoustic modules 14-1,14-2,14-3 secured to the structural element 40, the distances L1,L2,L3 separating the modules 14-1,14-2,14-3 pairwise from among the at least three modules all being different.

Different distances L1,L2,L3 are necessary so as to allow the location of an impact by temporal correlation, and therefore by triangulation, of the sound waves recorded by each of the three modules 14-1,14-2,14-3 at the moment at which the impact on the structural element 40 occurs, for example during a flight of the aircraft.

Of course, the invention also covers implementations of a detection device 10 in a structural element 40 extending substantially similarly in three dimensions, or in which more than three acoustic modules 14 are secured to the structural element 40, whatever the number of dimensions in which it principally extends.

Finally, the present invention also covers a method for detecting an impact on a composite material aircraft structural element 40.

This method comprises implementing a detection device 10 to detect an impact occurring on the structural element 40, especially during a flight of the aircraft.

This detection method also makes provision for the detection device 10 to be implemented to locate the impact detected on the structural element 40.

And, the detection method also makes provision for the detection device 10 to be implemented to evaluate the criticality of an impact detected on the structural element 40.

The detection method according to the invention is now described in respect of the detection of an impact on a composite material aircraft structural element 40.

The step prior to the implementation of this method comprises implanting the acoustic modules 14 of the detection device 10 in and/or on the structural element 40 to be monitored, as has been described earlier.

Then, before the use of the detection device, provision can be made for a calibration of the acoustic modules 14, for example with the aid of an acoustic hammer.

This calibration comprises measuring, for at least one gauged and targeted impact on the structural element 40, the energy level of the sound wave received by each acoustic module 14.

Thereafter, the position of each acoustic module 14 with respect to the impact point being known, the calibration makes it possible to establish mathematical functions giving the position and the energy level of an arbitrary impact as a function of the sound wave perceived by each acoustic module 14.

After this calibration, the detection device 10 is ready to be used.

In the application principally envisaged by the present invention, the acoustic modules 14 of the detection device 10 are used to record the sound waves travelling through the structural element 40 over the duration of a flight phase of the aircraft.

Of course, the invention is not limited to such a use and the detection device can also be used while the aircraft is parked or moving on the ground.

Prior to each new cycle of recording of the sound waves travelling through the structural element 40, a synchronization of the acoustic modules 14 of the detection device 10 is performed.

This synchronization is performed by the emission by the communication means 26 of the master acoustic module 14-1 of a radiofrequency signal 34 comprising a time base common to the set of modules of the device 10 towards the other acoustic modules 14-2,14-3 of the device 10.

During the flight, the method provides for a recording by the recording means 24 of each acoustic module 14-1,14-2,14-3 of the sound waves travelling through the structural element 40 over a determined duration, for example the duration of the flight.

After landing, the method provides for a transfer, by the communication means 26, of the sound waves recorded by each acoustic module 14-1,14-2,14-3 to the processing unit 30.

Thus, the data relating to the sound waves that have traveled through the structural element 40 during the flight of the aircraft are recovered by the processing unit 30, and preferably by way of the radiofrequency reader 32.

Subsequently, the method makes provision for analyzing the sound waves transferred so as to detect possible impacts occurring on the structural element 40 during the flight.

By virtue of various analyses of the sound waves recorded and transferred by the acoustic modules 14 (frequency spectrum, amplitude level, etc.) and of the formulae obtained by calibration, it is possible to evaluate the criticality of an impact occurring on the structural element 40, for example by comparison with respect to a threshold, and/or to locate an impact occurring on the structural element 40, for example with a view to a local inspection with an appropriate item of equipment.

As is apparent from the foregoing specification, the invention is susceptible of being embodied with various alterations and modifications which may differ particularly from those that have been described in the preceding specification and description. It should be understood that I wish to embody within the scope of the patent warranted hereon all such modifications as reasonably and properly come within the scope of my contribution to the art.

The invention claimed is:

1. A device for detecting an impact on a composite material structure of an aircraft, the detection device comprising:
   at least two acoustic modules mounted to the composite material structure of the aircraft, and configured to communicate wirelessly with each other, and
   a processing unit configured to communicate remotely and wirelessly with each of the acoustic modules,
   each acoustic module having:
      an acoustic sensor,
      electrical energy generating means,
      means for recording sound waves sensed by the acoustic sensor, and
      remote communication means configured to communicate with the processing unit,
   wherein the electrical energy generating means of the acoustic module includes a micro-kinetic generator for producing an electrical energy on the basis of the vibrations undergone by the composite material structure of the aircraft, and an accumulator for storing up the electrical energy produced by the mirco-kinetic generator.

2. The device for detecting an impact on a composite material structure according to claim 1, wherein at least one acoustic module acts as a master module, and includes a clock.

3. The device for detecting an impact on a composite material structure according to claim 2, wherein the remote communication means of the master acoustic module are configured to communicate with the other acoustic modules of the detection device.

4. A method for detecting an impact on a composite material structural element of an aircraft, the structural element being equipped with an impact detection device according to claim 1, the detection method implementing the detection device according to the following steps:
   emission by the communication means of a master acoustic module of a radio frequency signal comprising a time base common to the set of modules of the device towards the other acoustic modules of the device,
   recording by the recording means of each acoustic module of the sound waves travelling through the structural element over a determined duration, transferring, by the communication means, the sound waves recorded by each acoustic module to the processing unit, analyzing the transferred sound waves so as to detect any impacts occurring on the structural element.

5. The method for detecting an impact on a composite material structural element of an aircraft according to claim 4, in which the step of analyzing the transferred sound waves comprises a step of evaluating a criticality of an impact occurring on the structural element.

6. The method for detecting an impact on a composite material structural element of an aircraft according to claim 4, in which the step of analyzing the transferred sound waves comprises a step of locating an impact occurring on the structural element.

7. The method for detecting an impact on a composite material structural element of an aircraft according to claim 4, in which the detection device is implemented during a flight of the aircraft.

8. An aircraft structure comprising a composite material structural element, the aircraft structure comprising the structural element being equipped with an impact detection device according to claim 1.

9. The aircraft structure according to claim 8, wherein the acoustic modules are fastened to a surface of the structural element.

10. The aircraft structure according to claim 8, wherein the acoustic modules are provided in the structural element.

11. The aircraft structure according to claim 8, wherein at least one acoustic module is fastened to a surface of the structural element, and wherein at least one acoustic module is provided in the structural element.

12. The aircraft structure according to claim 8, wherein the structural element extends principally in one dimension and wherein the detection device comprises only a first acoustic module secured to a first end of the structural element, and a second acoustic module secured to a second end of the structural element.

13. The aircraft structure according to claim 8, wherein the structural element extends principally in two dimensions, and wherein the detection device comprises at least three acoustic modules secured to the structural element, the distances separating the modules pairwise from among the at least three modules all being different.

* * * * *